(12) United States Patent
Frisken et al.

(10) Patent No.: US 10,470,655 B2
(45) Date of Patent: Nov. 12, 2019

(54) OCULAR METROLOGY EMPLOYING SPECTRAL WAVEFRONT ANALYSIS OF REFLECTED LIGHT

(71) Applicant: Cylite Pty Ltd, Notting Hill (AU)

(72) Inventors: Steven James Frisken, Vaucluse (AU); Grant Andrew Frisken, Mitcham (AU)

(*) Notice: Subject to any disclaimer, the term of this patent is extended or adjusted under 35 U.S.C. 154(b) by 101 days.

(21) Appl. No.: 15/881,809

(22) Filed: Jan. 29, 2018

(65) Prior Publication Data

US 2018/0146851 A1    May 31, 2018

Related U.S. Application Data

(63) Continuation of application No. 14/899,559, filed as application No. PCT/AU2014/000637 on Jun. 20, 2014, now Pat. No. 9,913,579.

(30) Foreign Application Priority Data

Jun. 20, 2013    (AU) ................................ 2013902254

(51) Int. Cl.
*A61B 3/10*    (2006.01)
*A61B 3/107*    (2006.01)
(Continued)

(52) U.S. Cl.
CPC .......... *A61B 3/1015* (2013.01); *A61B 3/0025* (2013.01); *A61B 3/107* (2013.01);
(Continued)

(58) Field of Classification Search
CPC ..... A61B 3/1015; A61B 3/1025; A61B 3/107; A61B 3/117; A61B 3/14; A61B 3/0025;
G02B 27/283; G02B 27/1013; G01J 9/02; G01J 2009/0238; G01J 2009/0219; G01B 9/02044; G01B 9/02041; G01B 9/02039; G01B 9/02027; G01B 2290/70; G01B 9/02091

See application file for complete search history.

(56) References Cited

U.S. PATENT DOCUMENTS 9,737,204 B2    8/2017    Wall et al.
2010/0225883 A1    9/2010    Ho
(Continued)

FOREIGN PATENT DOCUMENTS

CN    102589440    7/2012

*Primary Examiner* — Jack Dinh
(74) *Attorney, Agent, or Firm* — Darren Gardner

(57) ABSTRACT

Method and systems are presented for analysing a wavefront using a spectral wavefront analyser to extract optical phase and spectral information at a two dimensional array of sampling points across the wavefront, wherein the relative phase information between the sampling points is maintained. Methods and systems are also presented for measuring an eye by reflecting a wavefront of an eye and measuring the wavefront at a plurality of angles to provide a map of the off-axis relative wavefront curvature and aberration of the eye. The phase accuracy between wavelengths and sample points over a beam aperture offered by these methods and systems have a number of ocular applications including corneal and anterior eye tomography, high resolution retinal imaging, and wavefront analysis as a function of probe beam incident angle for determining myopia progression and for designing and testing lenses for correcting myopia.

21 Claims, 9 Drawing Sheets

(51) Int. Cl.
    *A61B 3/117*     (2006.01)
    *A61B 3/14*     (2006.01)
    *A61B 3/00*     (2006.01)
    *G01B 9/02*     (2006.01)
    *G02B 27/28*     (2006.01)
    *G02B 27/10*     (2006.01)
    *G01J 9/02*     (2006.01)
    *G02C 7/02*     (2006.01)

(52) U.S. Cl.
    CPC ............ *A61B 3/1025* (2013.01); *A61B 3/117* (2013.01); *A61B 3/14* (2013.01); *G01B 9/02027* (2013.01); *G01B 9/02039* (2013.01); *G01B 9/02041* (2013.01); *G01B 9/02044* (2013.01); *G01B 9/02091* (2013.01); *G01J 9/02* (2013.01); *G02B 27/1013* (2013.01); *G02B 27/283* (2013.01); *G01B 2290/70* (2013.01); *G01J 2009/0219* (2013.01); *G01J 2009/0238* (2013.01); *G02C 7/027* (2013.01); *G02C 2202/24* (2013.01)

(56) References Cited

U.S. PATENT DOCUMENTS

| | | |
|---|---|---|
| 2013/0027711 A1 | 1/2013 | Hajian |
| 2014/0013980 A1 | 1/2014 | Veres et al. |
| 2014/0139804 A1 | 5/2014 | Ehrmann et al. |

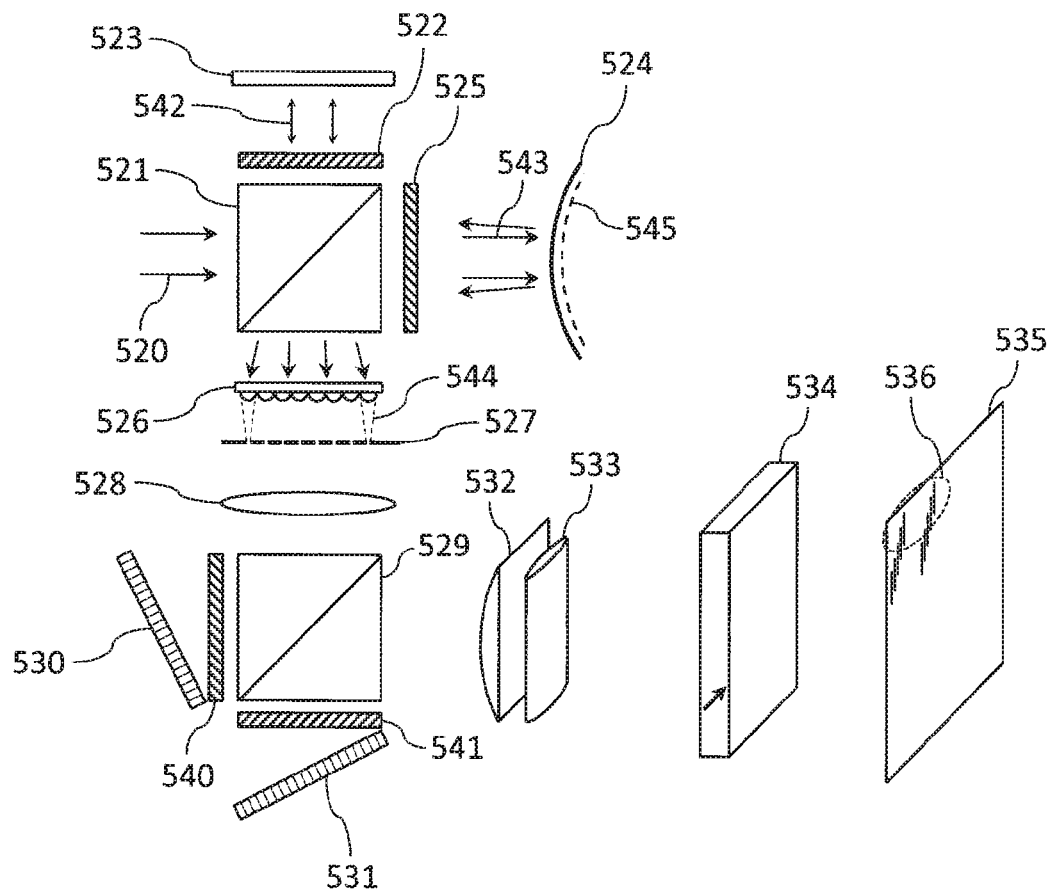
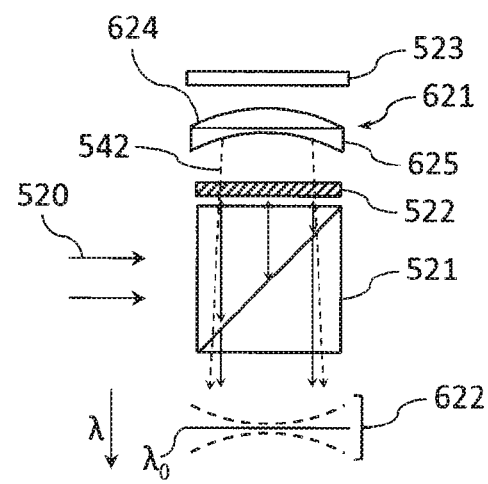
FIG 5
FIG 6

OCULAR METROLOGY EMPLOYING SPECTRAL WAVEFRONT ANALYSIS OF REFLECTED LIGHT

CROSS REFERENCE TO RELATED APPLICATIONS

The present application is a continuation of U.S. patent application Ser. No. 14/899,559 filed 18 Dec. 2015 which was a national stage entry of PCT/AU2014/000637 filed 20 Jun. 2014, the contents of each of which are incorporated herein by reference. The present application claims priority from Australian provisional patent application no 2013902254, filed on 20 Jun. 2013, the contents of which are incorporated herein by reference.

FIELD OF THE INVENTION

This invention relates to the metrology of optically reflective and scattering media, and to the field of hyperspectral imaging and wavefront analysis. The invention has been developed primarily for metrology of the human eye and will be described hereinafter with reference to this application. However it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Measurements of optical components and in particular the human eye have been addressed by a range of different instruments which have been able to provide information regarding different aspects of the eye's morphology and function as well as identification of various anomalies. Measuring the profile of the surface of the eye is of particular interest in applications where contact lenses need to be fitted, and as the range and functionality of contact lenses increases the requirement for accurate measurement of the surface topography over a larger area is becoming increasingly important. Other measurements that can be made include wavefront analysis, which is a phase-based measurement of the optical properties of the eye, i.e. eye function. Measurement of the various features of the anterior segment of the eye can be of great value in surgical applications. Considerable advances have been made in imaging the retina of the eye, and Optical Coherence Tomography (OCT) has enabled analysis of various eye structures in three dimensions through a scanning approach using information contained within the intensity and phase of reflected light.

FIG. 1 shows in schematic form a Placido disc topographer capable of calculating the elevation and curvature of a human cornea in vivo. A series of concentric illuminated rings 100 are reflected specularly from the target cornea 101, and an image of the reflections is projected by a lens system 102 onto an imaging sensor 103. Software is used to process the captured image to identify the ring reflections and the corresponding physical rings. Using the known geometry of the rings 100 and the lens system 102 a reverse ray trace 104 is performed between each ring image and the corresponding physical ring to determine the slope of the corneal surface at each reflection point, starting from the corneal apex 105. An 'arc-step' algorithm is used to calculate the slope, curvature and axial depth of the next ring reflection point along each radial.

FIG. 2 shows in schematic form a 'push broom' hyperspectral imager capable of spectrally analysing the intensity of light at a number of points along a slit aperture 222. A slit aperture 222 is used to analyse a linear portion of a sample 221, such as an image created by a telescopic or other imaging system. A collimating lens 223 directs the light collected by the slit aperture to a dispersive element such as a grating 225 which angularly disperses the wavelength components of the light, and a focusing lens 224 focuses each wavelength component onto a separate position along the wavelength axis of a focal plane array 226, where the information can be collected and analysed. A full hyperspectral image can be obtained by scanning the sample 221 relative to the slit aperture 222. Hyperspectral imaging has also been extended to two dimensional 'single shot' applications where light intensity at different wavelengths across an area is measured 'single shot' rather than in a scanning fashion.

Hyperspectral imaging only gathers intensity-related information, and any phase information is lost. It is of limited value to ocular metrology, and biological applications have been generally limited to understanding spectroscopic features such as oxygenation of blood, which is revealed in an absorption or fluorescence signature.

FIG. 3 shows in schematic form a wavefront analyser for determining the wavefront aberrations of an eye. An incoming known beam or wavefront 321, generally but not necessarily monochromatic, is transmitted through a beam splitter 322 to an eye under test 324 where the beam is focused by the eye's optical power 323, ideally onto or close to the retina 325. A small reflected component is then collimated by the eye's optical power and separated from the incoming beam 321 by the beam splitter 322 to form an outgoing wavefront 326, which contains information on residual optical power and aberrations of the eye 324.

The outgoing wavefront 326 is analysed with a Shack-Hartmann analyser 327 which, as shown in the enlargement in FIG. 3a, consists of a micro lens array 331 that samples the wavefront across a predetermined grid and focuses it onto a focal plane array 333. The positions of the image spots 334 formed by each micro lens can be used to estimate the slope 335 of the wavefront 326 at each sampling point, and if the slopes can be determined with sufficient accuracy and if the changes between the sampling points are not too great, it is possible to reconstruct the actual phase 328 of the wavefront across the sampling points. Multi-spectral wavefront analysers have been proposed for determining the dispersive properties of an optical component, e.g. longitudinal chromatic aberration of the eye, as discussed for example in P. Jain and J. Schwiegerling 'RGB Shack-Hartmann wavefront sensor', J. Modern Optics 55 (2008) 737-748, and in S. Manzanera et al 'A wavelength tunable wavefront sensor for the human eye', Optics Express 16 (2008) 7748-7755. However relative phase information between the different wavelengths is not obtained.

Many approaches to the analysis of the eye have relied on variations of a technique known as optical coherence tomography (OCT), which is able to provide tomographic data on eye structure and has been incorporated into many ocular instruments. There are two main approaches employed, time domain OCT and spectral domain OCT. In time domain OCT coherence properties of a partially coherent source such as a Superluminescent Light Emitting Diode (SLED) with a coherence length of several microns are utilised by imaging light reflected from a sample and interfering the image or a single point within the image with a reference beam provided by the same source, but with a time-varying path length. At a specific depth in the sample corresponding to the path length delay, an interference envelope of fringes will be detected in the combined back-reflected signal, allowing the reflection profile in the depth dimension to be reconstructed. Commonly this is done for only a single sample point at a time, and the corresponding scan of depth is known as an 'A scan'. A variation of this technique, known as linear OCT, provides for the A scan to be captured in a single shot by appropriate angling of the reference and sample beams and detection of the fringes along a focal plane array. In each case the sample points can be scanned in an orthogonal dimension to provide a two-dimensional 'B scan' or even a complete three-dimensional scan.

Instead of scanning a delay line, spectral domain OCT techniques analyse the reflected light by interfering it with a reference beam, either as a time-varying function of wavelength (swept source OCT) or by dispersing the different wavelengths with a grating or other spectral demultiplexer and detecting them simultaneously along a detector array. The spectral domain information is the Fourier transform of the spatial (depth) reflection profile, so the spatial profile can be recovered (within the limitations of the technique) by a Fast Fourier Transform. Modern computational techniques enable fast A scans that can be scanned in two axes, with resonant scanning mirrors for example, to give complete high resolution scans at refresh rates which are a trade-off between the clinically permissible optical power, resolution and signal-to-noise requirements. It is known that in a scanning system utilising OCT it is difficult to achieve high accuracy relative measurements between the different sample points because of the micron level movements of the human eye in vivo that occur over period of a scan, which is typically of order one second.

Nguyen et al (Optics Express 21 (2013) 13758-13772) have proposed an OCT system based on combining an interferometer with a modified hyperspectral imaging system that is able to measure multiple A scans across an image plane. However because there is no calibration or method specified to guarantee phase relationships, this system appears to be unable to maintain relative phase information between sampling points or wavelengths.

OBJECT OF THE INVENTION

It is an object of the present invention to overcome at least one of the limitations of the prior art. It is an object of the present invention in its preferred form to provide systems and methods for making accurate measurements relying on optical phase in living biological samples, especially samples such as eyes which may be prone to motion artefacts.

SUMMARY OF THE INVENTION

According to a first aspect of the present invention there is provided an optical system for analysing a wavefront, said system comprising a spectral wavefront analyser adapted to extract optical phase and spectral information at multiple sampling points across said wavefront, wherein the relative phase information between said multiple sampling points is maintained and wherein said multiple sampling points form a two dimensional sampling array.

The two dimensional sampling array preferably comprises a plurality of beamlets formed by a micro lens array.

In preferred embodiments the wavefront is obtained by reflection or transmission of a probe beam from or through a sample.

The system is preferably adapted to extract the optical phase and spectral information from the multiple sampling points in a single acquisition, to reduce artefacts caused by motion of the sample.

In preferred embodiments the system comprises a processor adapted to process the optical phase and spectral information to provide a tomographic profile of the sample, or to provide a measurement of the corneal topography of an eye, or to determine the profile of one or more interfaces in the anterior segment of an eye.

The system preferably comprises an interferometer, and the optical phase and spectral information are extracted by interfering the wavefront with a reference beam. The interferometer preferably comprises one or more dispersive elements for dispersing the reference beam. Preferably, at least one of the one or more dispersive elements comprises a grating. The system preferably comprises polarisation optics adapted to orthogonally polarise the reference and probe beams and to analyse the resultant polarisation state after the wavefront has been interfered with the reference beam. In preferred embodiments the polarisation optics are adapted to analyse more than one polarisation state to provide a balanced detection system.

According to a second aspect of the present invention there is provided a method for analysing a wavefront, said method comprising the step of extracting optical phase and spectral information at multiple sampling points across said wavefront, wherein the relative phase information between said multiple sampling points is maintained and wherein said multiple sampling points form a two dimensional sampling array.

In preferred embodiments the two dimensional sampling array comprises a plurality of beamlets formed by a micro lens array.

The wavefront is preferably obtained by reflection or transmission of a probe beam from or through a sample.

The optical phase and spectral information is preferably extracted from the multiple sampling points in a single acquisition, to reduce artefacts caused by motion of the sample.

Preferably, the method further comprises the step of processing the optical phase and spectral information to provide a tomographic profile of the sample, or to provide a measurement of the corneal topography of an eye, or to determine the profile of one or more interfaces in the anterior segment of an eye.

In preferred embodiments the optical phase and spectral information is extracted by interfering the wavefront with a reference beam. The reference beam is preferably dispersed by one or more dispersive elements. Preferably, at least one of the one or more dispersive elements comprises a grating. In preferred embodiments the method further comprises the steps of: orthogonally polarising the reference and probe beams; and analysing the resultant polarisation state after the wavefront has been interfered with the reference beam. Preferably, more than one polarisation state is analysed to provide balanced detection of the wavefront.

According to a third aspect of the present invention there is provided a method for measuring an eye, said method comprising the steps of:
obtaining a wavefront by reflecting a probe beam off an eye; and measuring said wavefront at a plurality of angles to provide a map of the off-axis relative wavefront curvature and aberration of said eye.

In certain embodiments the plurality of angles is provided by a dispersive element and the wavefront is measured at a plurality of wavelengths. Alternatively the plurality of angles is provided by reflecting the wavefront off a scanning mirror.

In preferred embodiments the method further comprises the step of determining the optical depth of the eye through identification of predetermined optical frequencies with respective reflection points and determining the corresponding relative optical depth associated with each optical frequency.

According to a fourth aspect of the present invention there is provided an optical system for measuring an eye, said system comprising:

means for obtaining a wavefront by reflecting a probe beam off an eye; and means for measuring said wavefront at a plurality of angles to provide a map of the off-axis relative wavefront curvature and aberration of said eye.

In certain embodiments the means for measuring the wavefront comprises a dispersive element for providing the plurality of angles, and is adapted to measure the wavefront at a plurality of wavelengths. Alternatively the means for measuring said wavefront comprises a scanning mirror for reflecting the wavefront at the plurality of angles.

Preferably, the system is adapted to determine the optical depth of the eye through identification of predetermined optical frequencies with respective reflection points and determining the corresponding relative optical depth associated with each optical frequency.

According to a fifth aspect of the present invention there is provided a method for designing a lens for correcting myopia, said method comprising the steps of:

obtaining a wavefront by reflecting a probe beam off an eye;

measuring said wavefront at a plurality of angles to provide a map of the relative wavefront curvature across said eye; and utilising on-axis and peripheral wavefront data to design said lens such that, in use, said lens corrects myopia of said eye for on-axis wavefronts and focuses peripheral wavefronts on or behind the retina of said eye.

According to a sixth aspect of the present invention, there is provided a system for designing a lens for correcting myopia, said system comprising:

means for obtaining a wavefront by reflecting a probe beam off an eye;

means for measuring said wavefront at a plurality of angles to provide a map of the relative wavefront curvature across said eye; and means for utilising on-axis and peripheral wavefront data to design said lens such that, in use, said lens corrects myopia of said eye for on-axis wavefronts and focuses peripheral wavefronts on or behind the retina of said eye.

According to a seventh aspect of the present invention there is provided a method for testing a lens for correcting myopia, said method comprising the steps of:

obtaining a wavefront by reflecting a probe beam off an eye when said lens is in place such that said probe beam passes through said lens;

measuring said wavefront at a plurality of angles to provide a map of the wavefront curvature across said eye and said lens in combination; and utilising on-axis and peripheral wavefront data to ascertain whether said lens is correcting the myopia of said eye for on-axis wavefronts and focusing peripheral wavefronts on or behind the retina of said eye.

According to an eighth aspect of the present invention there is provided a system for testing a lens for correcting myopia, said system comprising:

means for obtaining a wavefront by reflecting a probe beam off an eye when said lens is in place such that said probe beam passes through said lens;

means for measuring said wavefront at a plurality of angles to provide a map of the wavefront curvature across said eye and said lens in combination; and means for utilising on-axis and peripheral wavefront data to ascertain whether said lens is correcting the myopia of said eye for on-axis wavefronts and focusing peripheral wavefronts on or behind the retina of said eye.

According to a ninth aspect of the present invention there is provided a lens for correcting myopia, wherein said lens is designed using the method of the fifth aspect or the system of the sixth aspect, or tested using the method of the seventh aspect or the system of the eighth aspect.

According to a tenth aspect of the present invention there is provided an article of manufacture comprising a computer usable medium having a computer readable program code configured to operate the optical system according to the first or fourth aspects, or to operate the system according to the sixth or eighth aspects, or to implement the method according to the second, third, fifth or seventh aspects.

BRIEF DESCRIPTION OF THE DRAWINGS

Preferred embodiments of the invention will now be described, by way of example only, with reference to the accompanying drawings in which:

FIG. 5 illustrates in schematic form an optical train for an embodiment of the present invention, employing a reference beam to measure the phase of light interferometrically at a number of grid points and wavelengths;

FIG. 6 illustrates in schematic form an optical train for another embodiment of the present invention, including a reference arm where a wavelength dependent optical wavefront curvature is introduced into the reference beam;

DETAILED DESCRIPTION OF THE INVENTION

The present invention is directed to systems and methods for obtaining detailed optical metrology data of samples through the acquisition of accurate relative phase information between the wavelengths, and also spatially, across a multi-wavelength optical wavefront formed by reflection or transmission of an optical beam of known intensity and phase profile incident on a sample to be measured, wherein the optical scattering and/or reflective terms are able to be determined. The ability to extract optical phase and spectral information at multiple sampling points can be exploited to provide measurement systems configurable to measure a range of parameters of the human eye using techniques such as high accuracy corneal topography, grid-based anterior eye tomography, line-based anterior eye tomography, high resolution retinal imaging, wavefront analysis as a function of incident angle of a probe beam for determination of myopia progression, and single shot acquisition of ps resolved images for monitoring retinal ablation.

Figure 1:
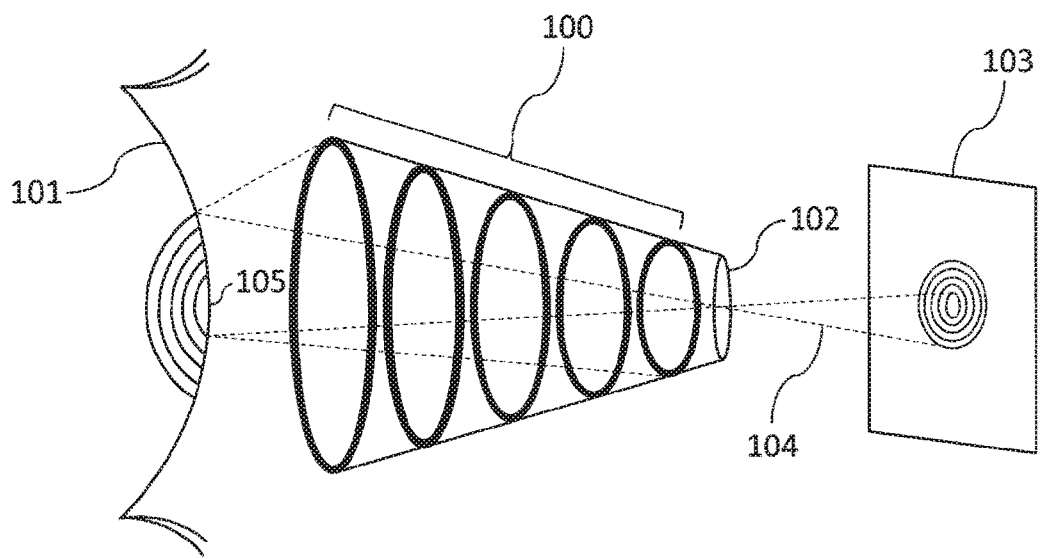
FIG. 1 illustrates in schematic form a Placido disc topographer capable of calculating the elevation and curvature of a human cornea in vivo.
Figure 2:
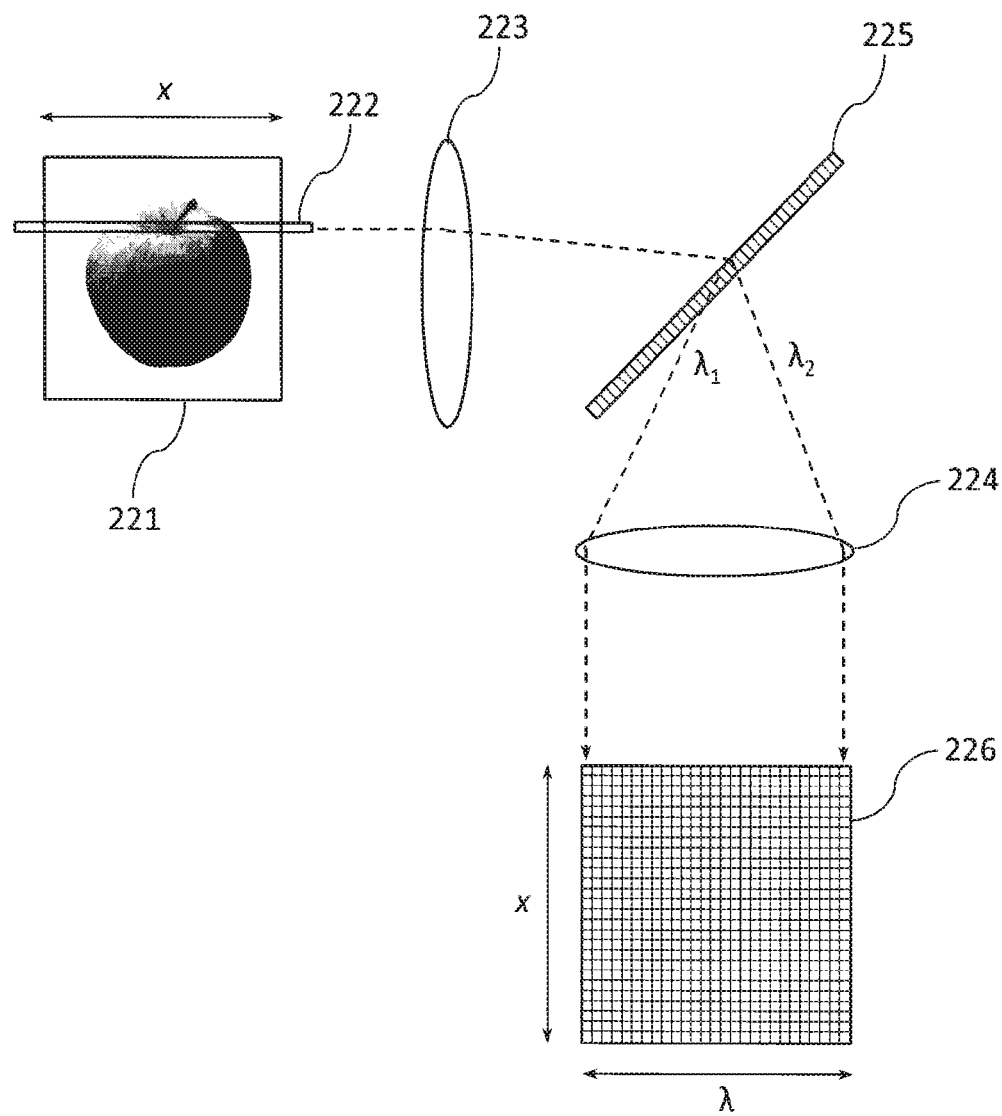
FIG. 2 illustrates in schematic form a 'push broom' hyperspectral imager capable of spectrally analysing the intensity of light at a number of points along a slit aperture.
Figure 3:
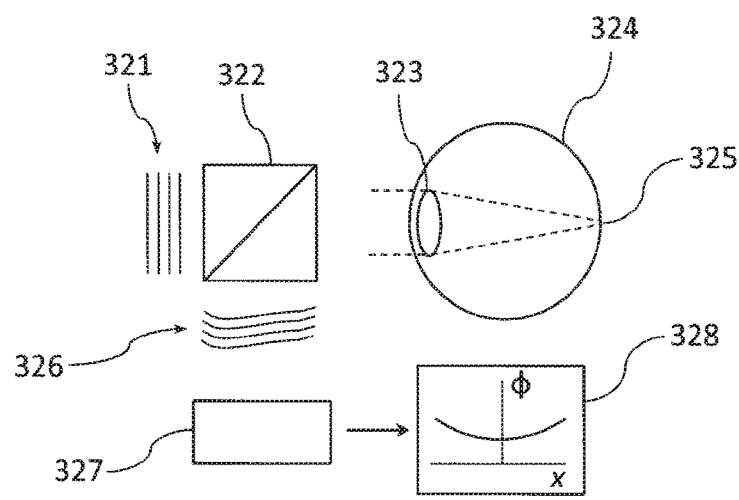
FIG. 3 illustrates in schematic form a wavefront analyser for determining the wavefront aberrations of an eye.
Figure 3A:
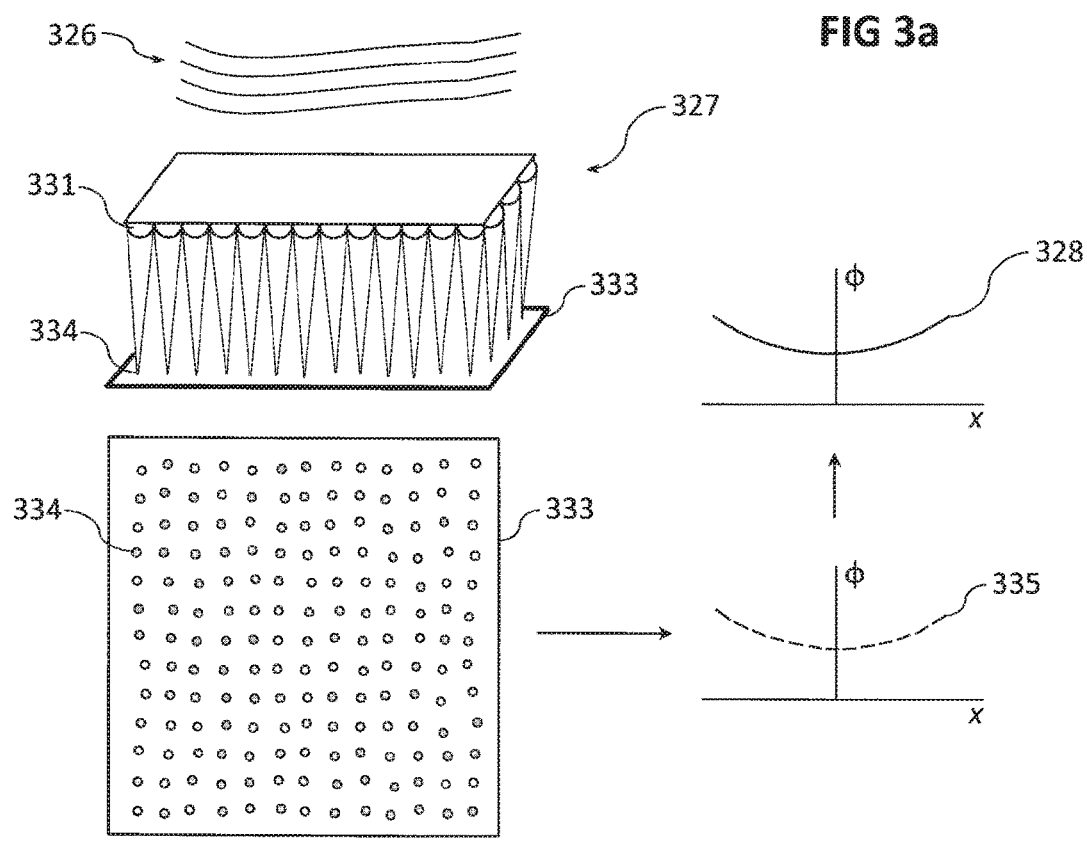
FIG. 3a shows an enlarged view of a portion of FIG. 3.
Figure 4A:
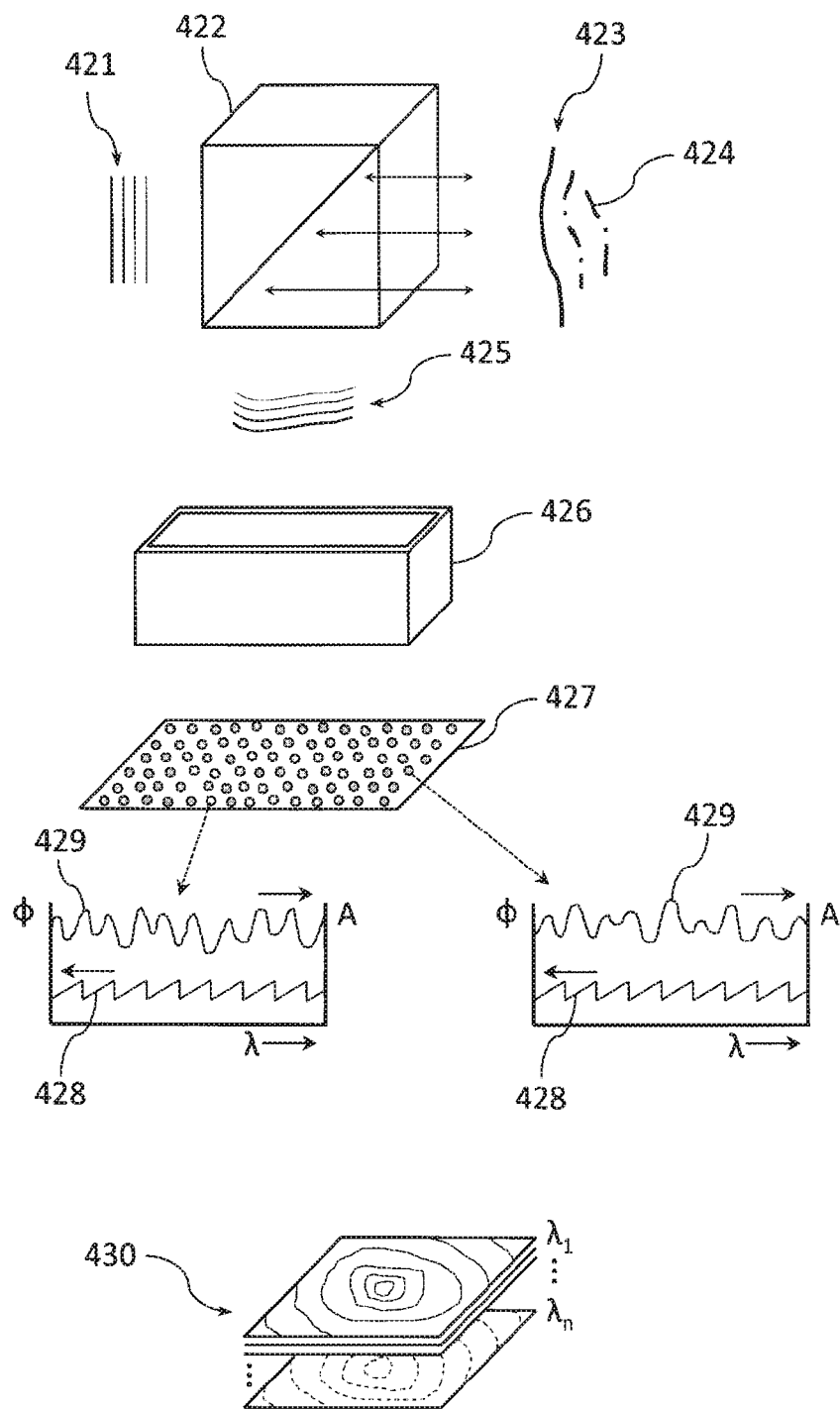
FIG. 4a is a conceptual diagram of a high spectral resolution hyperspectral wavefront analysis system according to an embodiment of the present invention.

FIG. 4a is a conceptual diagram of a high spectral resolution hyperspectral wavefront analysis system according to an embodiment of the present invention. A known multi-wavelength incoming wavefront 421, which may be planar or spherical for example, is passed through a beam splitter 422 of either a polarisation or power splitting type and reflected off a sample under test 423 which may consist of a number of distributed or discrete reflection layers or interfaces 424, such as may be found in the anterior segment of an eye. Information on the morphology and reflectivity of the sample is coded into the shape and spectral response of the reflected wavefront 425, which is separated from the incoming wavefront 421 by the beam splitter 422. Similar to Shack-Hartmann analysis the wavefront 425 is sampled over a two dimensional grid 427, however in this case the sampling is performed by a spectral wavefront analyser 426 so as to produce optical phase and spectral information in the form of sampled phase 428 and amplitude 429 as a function of wavelength $\lambda$ for each point in the grid 427, for subsequent analysis by a processor equipped with suitable computer readable program code. The sampling is preferably chosen to ensure continuity and accurate calibration of the relative phase and amplitude contours 430 across both spatial dimensions, and also across wavelength, so that the sampled phase and amplitude data can be determined even in the presence of test sample movement that would be expected for clinical in vivo measurements.

Figure 4B:
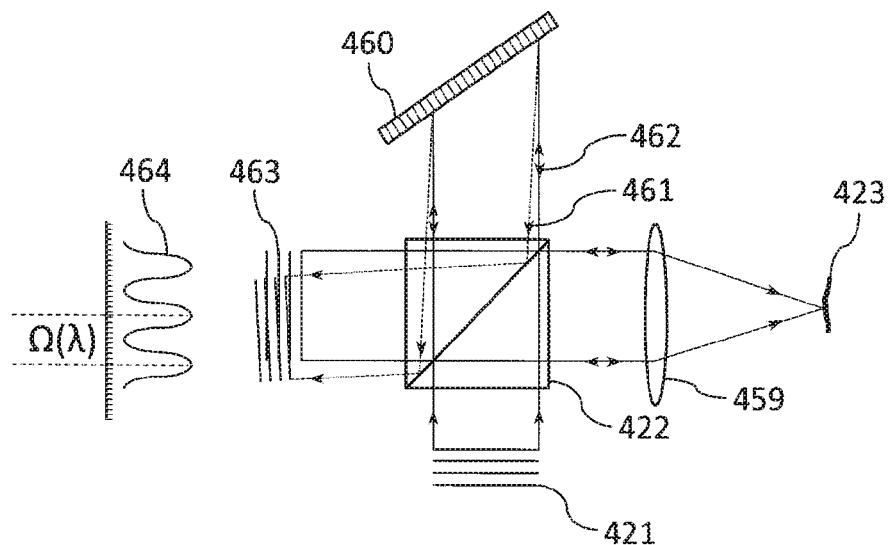
FIG. 4b illustrates a technique for measuring the spectral phase and amplitude response of reflected light.

FIG. 4b illustrates a technique for measuring the spectral phase and amplitude response of light reflected from a sample 423 at a single point for the purposes of clearly explaining the principles of operation to be used in the following embodiments. One portion of a planar multi-wavelength wavefront 421 is directed via a beam splitter 422 to the sample 423 via a focusing lens 459, and a second portion (a reference wavefront) is directed to a grating 460. Light from the reference wavefront is dispersed 461 and 462 according to wavelength and combined with the multi-wavelength wavefront 463 reflected from the sample 423 to form fringe patterns 464 with periods $\Omega(\lambda)$ corresponding to the wavelengths $\lambda$ due to the varying angles associated with the dispersion of the grating 460. The optical frequencies of the light reflected from the sample have been transformed to spatial frequencies that can be analysed by Fourier analysis of the resultant interference fringes using a processor equipped with suitable computer readable program code. In this particular embodiment the grating 460 is operating in reflection and at near Littrow reflection angle, although these choices are not critical as several other configurations are possible.

FIG. 5 illustrates in schematic form the optical train of a spectral wavefront analyser according to an embodiment of the present invention, employing a reference beam to measure the phase of light interferometrically at a plurality of wavelengths across a two dimensional grid of sample points, i.e. a two dimensional sampling array.

A known multi-wavelength incoming wavefront 520, for example from a SLED or a swept wavelength source is split into a reference beam 542 and a probe beam 543, according to the polarisation state of the incoming wavefront (for example elliptical), by a polarisation beam splitter (PBS) 521. The reference beam 542 is passed through a quarter waveplate 522 and reflected from a minor 523, while the probe beam 543 is passed through another quarter waveplate 525 and reflected from a sample under test 524, which again may consist of a number of distributed or discrete reflection layers or interfaces 545 such as may be found in the anterior segment of an eye. The reference and probe beams are recombined through polarisation multiplexing at the PBS 521 and directed towards a micro lens array 526 and an optional aperture array 527 to create a two dimensional sampling array (effectively the waists of the beamlets 544). The aperture array 527 is optional, but improves the spatial resolution of the system and improves the isolation between neighbouring beamlet measurements. The multi-wavelength beamlets are collimated by a lens 528 (for a transmissive configuration as shown) and directed to a second PBS 529 which separates the beamlets into reference and probe components. The two components are directed through respective polarisation waveplates 540 and 541 onto corresponding diffraction gratings 530 and 531 which can be aligned to have identical or opposite sign dispersive directions according to their orientation. Alternatively, for applications requiring less dispersion it is possible to use conventional prisms or other dispersive techniques. The dispersed reference and probe beamlets are recombined by the PBS 529, and an optical train consisting of cylindrical lenses 532 and 533 or a spherical lens relays the recombined image through one or more polarisation analysing elements 534 such as a $YVO_4$ walk-off plate (as shown) or another PBS before being detected at a focal plane array 535. Each beamlet forms a pair of images 536 that are tightly focused orthogonal to the dispersive axis and spread in the dispersive axis. If the dispersions of the gratings 530 and 531 are oppositely aligned, the optical train is configured to create a far-field image of the reference and probe beamlets which will interfere once their polarisation has been analysed. If we consider a single wavelength of light, the frequency of a spatial oscillation within each beamlet will correspond to the wavelength of the light, and the phase relative to the reference beam can be obtained via the locations of the nulls and maxima corresponding to that frequency. It will be appreciated by one skilled in the art that the superposition of multiple wavelength fringe patterns can be analysed by Fourier transform techniques with a processor equipped with suitable computer readable program code, as each wavelength corresponds to a specific spatial oscillation. An example Fourier transform technique is described in the co-pending Patent Cooperation Treaty patent application entitled 'Wavefront Analyser' and filed on even date, the contents of which are incorporated herein by reference. Additionally, if the far-field images have curvature or aberration this can be corrected in the mathematical analysis, reducing the requirement for precision optical components and tolerances, and therefore significantly reducing the expense of the instrumentation for widespread clinical applications. In the specific case where there is a linear correlation between the optical frequencies and the spatial frequencies, the summation of the spatial frequencies can create a correspondence between depth of a sample reflection point and the spatial interference envelope.

In an alternative embodiment the sample and reference arms are dispersed after being re-combined at the PBS 529, and focused in the dispersive axis. This has the effect of associating a linear array of pixels with each beamlet, where each pixel of the array corresponds to a specific wavelength, leading to a two-dimensional matrix of samples with each sample beamlet measured with its corresponding linear array. In some cases this spectrometer-like approach may provide a better signal-to-noise ratio, but it is more difficult to correct for aberrations of the optical setup as it requires each wavelength to be focused as tightly as possible, which is difficult to achieve without considerable complexity in the imaging optics.

In yet another embodiment the one or more polarisation analysing elements 534 are adapted to analyse more than one polarisation state of the recombined image, to provide a balanced detection system.

FIG. 6 shows in schematic form an alternative embodiment where the reference arm of the optical train from FIG. 5 is modified to introduce a wavelength dependent optical wavefront curvature into the reference beam 542. In this embodiment the reference beam polarisation component of an incoming beam 520 is passed though a compound lens 621 comprising a positive power element 624 and a negative power element 625 composed of glasses with different chromatic dispersions. The compound lens 621 introduces wavefront curvature 622 varying as a continuous function of wavelength $\lambda$, and is designed to have effectively null optical power at a predetermined wavelength $\lambda_0$.

Figure 7:
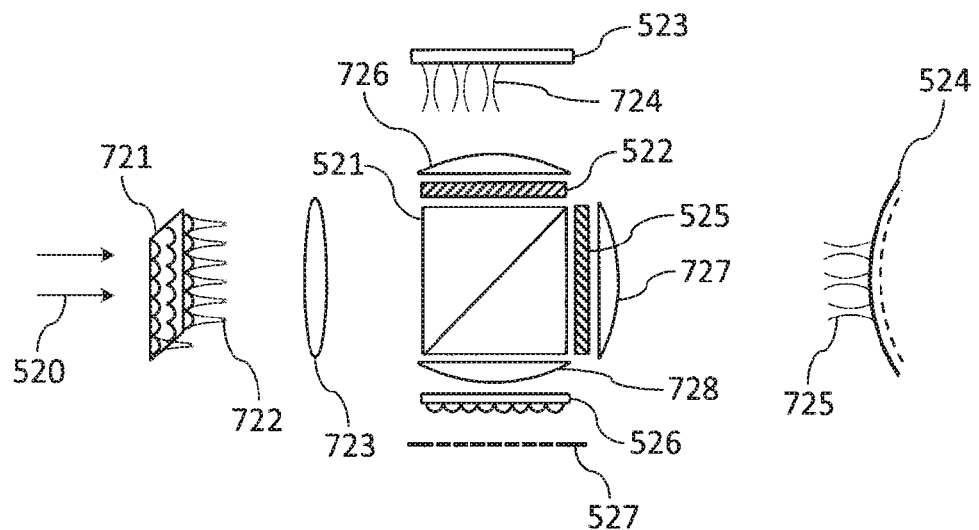
FIG. 7 shows how an incoming wavefront can be divided into a two dimensional array of beamlets.

FIG. 7 shows in schematic form another variation of the spectral wavefront analyser shown in FIG. 5 in which an incoming wavefront is divided into a two dimensional array of beamlets. An incoming known multi-wavelength beam 520 is passed through a spherical micro lens array 721 or a pair of cylindrical micro lens arrays to create an appropriate divergence grid, i.e. an array of sampling/reference points 722 corresponding to the beamlet waists. These beamlet waists are relayed through an appropriate optical train of lenses 723, 726 in the reference arm, and a similar train of lenses 723, 727 in the probe arm which includes a sample under test 524. Corresponding wavefronts with beamlets near waist (724 and 725) are created in each arm, which in turn are relayed via the PBS 521 and a lens 728 to the micro lens array 526, which serves to increase the numerical aperture of each spot (and hence reduce the spot size), before proceeding through the remainder of the spectral wavefront analysis system depicted in FIG. 5. In this way each of the probe beamlets corresponds to processing through a single micro lens, and unwanted scattering terms are avoided via rejection at the aperture array 527.

It should be emphasised that the use of a two-dimensional array of sample points provides the advantage of being able to detect in a single shot, and hence with minimal motion artefacts, the relative phase and amplitude across the spectrum of a beam reflected from an eye or other sample, allowing the reconstruction of the tomographic features to high precision, and/or measurement of the wavefront across the beam. If the exposure is too long such that there is relative sample movement within the acquisition time, then the detected fringes will be reduced in contrast but their corresponding position will not be affected. This fringe fading effect can be ameliorated by using a single short optical pulse during the acquisition period.

The phase accuracy between wavelengths and sample points over a beam aperture that results from the maintenance of relative phase information in the above described spectral wavefront analysis techniques can be exploited in the development of instruments with multiple applications including digital holographic reconstruction of high resolution two-dimensional and three-dimensional microscopy, accurate surface and layer topography, and new techniques in wavefront analysis of the eye as will be described below.

Figure 8:
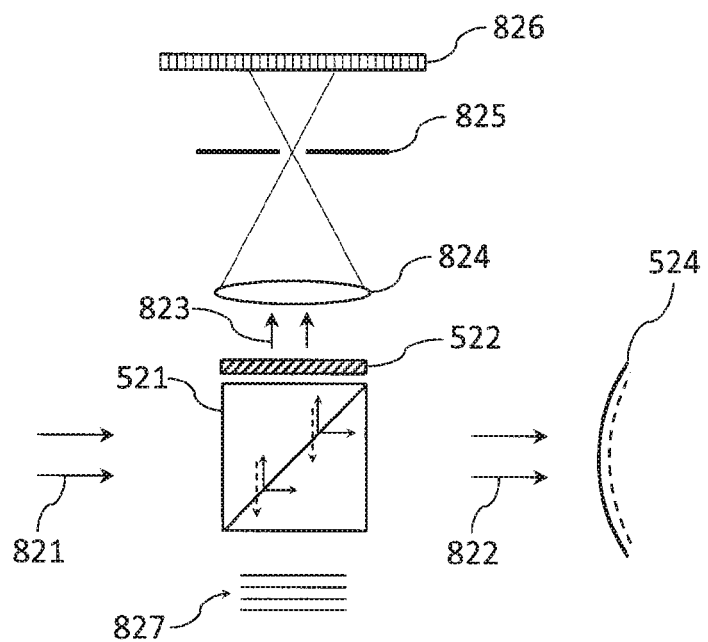
FIG. 8 illustrates the use of a reference wavefront with a spatial profile designed to be that of a model eye at some wavelength, to reduce the range of phase variations that need to be tracked over a measurement aperture.

FIG. 8 shows, according to one aspect of the present invention, a technique for approximating the wavefront reflection from the front surface of a model eye in the reference arm of an interferometer. An incoming nominally planar wavefront 821 is split into probe and reference beams 822 and 823 by a polarisation beam splitter 521. The reference beam 823 is passed through a quarter waveplate 522 and focused by a lens 824 through an aperture 825. Due to the use of the refractive optical element 824, the optical path lengths for all beam paths are significantly equal at the aperture. The light diverges spherically from the aperture 825 but is retro-reflected by a reflection component 826 such as a planar diffractive optics component. This creates a spherically varying optical path length difference which can approximate the path length difference of the light which travels to the first specular reflection point of an eye or other sample 524 in the probe beam path 822. This leads to a significant reduction in the phase variation across the recombined wavefront 827, which can be more easily tracked without phase ambiguity in the remainder of the wavefront analysis system. It is possible to use more than one diffractive optics component 826, and also to use non-planar substrates for the diffractive optics component(s), which in turn allows more complicated depth profiles to be approximated. Additionally, for multi-wavelength wavefronts 821 the FIG. 8 apparatus can be used to create a wavelength-dependent wavefront curvature as described in relation to FIG. 6.

Figure 9:
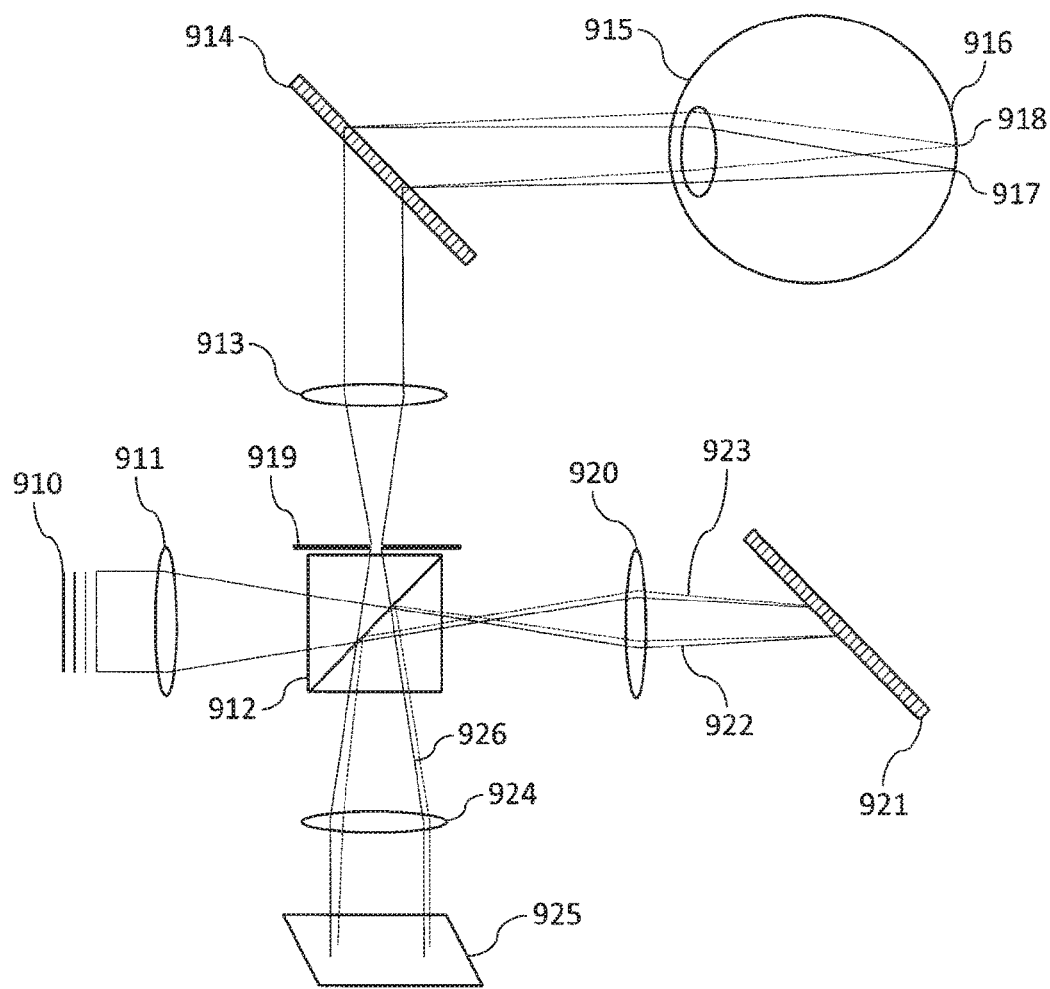
FIG. 9 shows how, according to another embodiment of the present invention, a series of off-axis wavefronts can be gathered with a single shot wavefront analyser.

FIG. 9 shows in schematic form the optical train of a spectral wavefront analyser according to another embodiment of the present invention, in which a series of off-axis wavefronts from a sample can be gathered with a single shot wavefront analyser. In this system each wavelength represents a different angle of incidence of an incoming beam 910 on an eye under test 915, and hence a different point on the retina 916 from which the sample wavefront to be analysed emanates.

Similar to the FIG. 5 embodiment, a multi-wavelength incoming wavefront of known characteristics 910 is split into two components by a beam splitter 912, which may be a polarisation beam splitter or a classical power beam splitter. One component (the probe beam) is relayed via the relay lenses 911 and 913 to a dispersive element such as a transmissive diffraction grating 914, which angularly disperses it into a number of trajectories depending on wavelength. The light in these trajectories is substantially focused by the power elements of an eye under test 915 to form a plurality of dispersed spots 917, 918 on the retina 916 of the eye. A small fraction of light from each spot is reflected back through the system and recombined by the diffraction grating 914 before being focused to an aperture 919 which can for example be a slit oriented orthogonal to the direction of the dispersive axis. The aperture 919 is positioned at the focal distance of a lens 924 that collimates the recombined light 926, at least in the axis orthogonal to the slit 919, before impinging on a focal plane array 925.

A second component of the incoming wavefront 910, i.e. the reference beam, is relayed via the relay lenses 911 and 920 to a diffraction grating 921, which angularly disperses it according to wavelength along different trajectories 922 and 923. This angularly multiplexed wavefront is relayed via the beam splitter 912 and lenses 920 and 924 to interfere with the combined wavefronts reflected from the eye under test 915, forming a plurality of interference patterns on a focal plane array 925, with the number of interference patterns determined by the number of wavelength components in the incoming wavefront 910.

In embodiments where the beam splitter 912 is a polarisation beam splitter the combination of the two beams can be effected by means of polarisation manipulations, e.g. insertion of quarter waveplates and a polarisation analysing element as described above with reference to FIG. 5 to analyse the relative phases of the two beams at each point in space.

As described in more detail in the above-mentioned co-pending PCT patent application entitled Wavefront Analyser' the resulting interference pattern at each wavelength corresponds to a spatial frequency in the direction of the dispersive axis, and the phase for each wavelength component can be reconstructed from the phase of the corresponding spatial frequency. The provision of dispersive elements in the reference and probe beam paths means that a large range of spatial frequencies can be used, from two pixels and upwards, and advantageously the phase can be unambiguously resolved for each wavelength. Although this is a single shot technique able to provide enhanced accuracy compared to scanning techniques through simultaneous capture of the entire wavefront for all off-axis trajectories at the eye 915, it is important to note that because it is an interferometric technique a short capture time is still important to reduce any fringe fading due to relative movement of the eye under test. Again, this can be facilitated by using short pulse illumination in addition to rapid shuttering of the focal plane array.

We now consider the application of the above described off-axis wavefront analysis to the diagnosis of myopia and to monitoring the progression or treatment of myopia. Recent studies have indicated the likelihood of a causal link between the off-axis focusing properties of the eye and the progression of myopia in some cases. It is important to consider ways to quantify this progression to aid understanding of the occurrence of myopia and for developing successful treatments. The apparatus disclosed in FIG. 9 allows the capture of a wide range of off-axis wavefronts around a predetermined axis from a beam reflected from the retina of an eye under test. By measuring the reflected wavefront at a plurality of angles, a map of the off-axis relative wavefront curvature and aberration of the eye can be obtained. Because a discrete set of beam angles at the eye is obtained via the dispersive elements, it is possible to track the phase accurately from one wavelength to the next and so cope with large variations in focus without requiring many mechanical adjustments to the measurement apparatus. Alternatively, instead of using a grating or other dispersive element to disperse the wavelengths, all wavelengths can be directed at varying angles by reflection off a scanning mirror positioned with respect to the optical train so as to create effective rotation of the beam about a point approximately one focal length away from the effective optical centre of the eye's lens. Again, this is described in more detail in the co-pending PCT patent application entitled 'Wavefront Analyser'.

Figure 11:
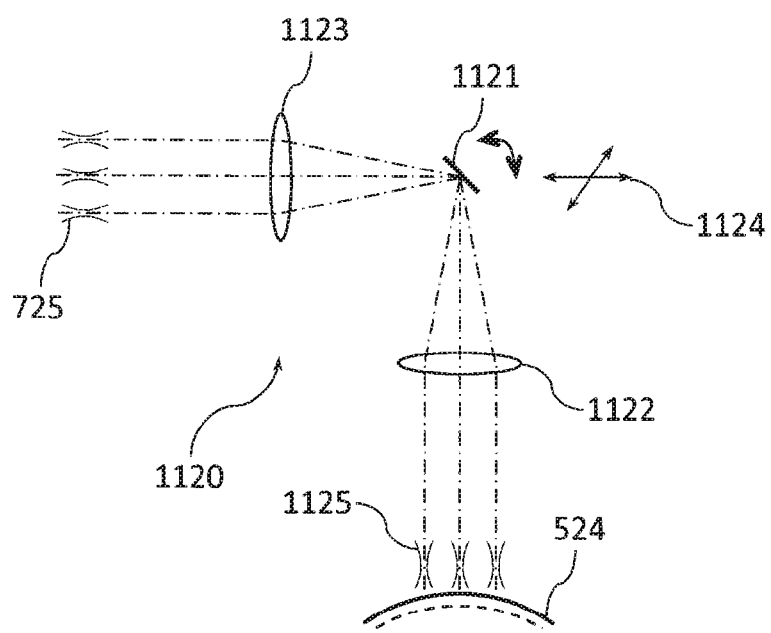
FIG. 11 illustrates an optical relay system suitable for adjusting the spatial position of a two dimensional array of beamlets on a sample.

A scanning mirror can also be beneficial in an optical relay system for extending the flexibility of the apparatus shown in FIG. 7 for projecting a grid of beam waists 725 onto a sample 524. As shown in FIG. 11, a suitable relay system 1120 comprises a scanning mirror 1121 and two optical power elements 1122 and 1123, which may for example be lenses or mirrors. The scanning mirror 1121 is placed at approximately the focal distance from at least one of the two optical power elements, preferably the element 1122 closer to the sample 524. An angular adjustment of the scanning mirror 1121 in either axis 1124 results in a lateral displacement of the re-imaged beam waists 1125 in the corresponding axis. The scanning mirror 1121 can be positioned at the focal point of both optical power elements 1122 and 1123 as shown in FIG. 11, in which case the relay system 1120 forms a 4F optical system, although the separation of the optical power elements can be varied if an adjustment to the trajectory of the beamlets 1125 is required Scanning the pixelated sample probe, i.e. the grid of beam waists, across a sample 524 in two or more exposures achieves a denser spatial sampling of the reflected sample wavefront without the requirement for a large scanning mirror or large angles to give complete imaging coverage of a 3D structure. Because the mirror 1121 is at a focal point in the relay system 1120 one can utilise small MEMS-type mirrors which are fast settling, compact and light weight to allow miniaturisation of the system. This gives considerable advantages for enhancing the metrology of reflective surfaces under test and also for allowing reconstruction of arbitrary scans across or through a sample.

Each exposure captures a two dimensional set of depth scans through a sample. Within each exposure the depth scans are acquired simultaneously, eliminating the issue of relative movement of the sample between scans. The exact location and angle of each beamlet relative to other beamlets in the grid 1125 does not change, and can be calibrated very precisely when the instrument is manufactured. This yields a significant advantage over scanning systems which acquire a single scan using a rotating mirror that is not at a focal point of a relay system, where, because the exact location of the mirror at any point cannot be measured precisely, a degree of uncertainty between any two measurements is introduced.

The set of depth scans acquired in each exposure can be segmented using standard image processing techniques to locate surfaces within a sample, which for ocular applications may include the anterior and posterior surfaces of the cornea. A mathematical surface model (such as a Zernike polynomial) can be fitted to the segmented surface data using standard surface fitting methods. Typically the time between exposures means that there will be some relative displacement or rotation between each set of data, due to either the movement of the scanning mirror or movement of the sample. The data from subsequent exposures can be corrected for this movement by registering the surface data with the mathematical model from the initial exposure. The segmented data points are rotated and/or displaced about all three axes and the distance from the displaced/rotated surface points to the initial mathematical surface is minimised, using standard optimisation techniques, to determine the optimal alignment between the surfaces. The mathematical surface model can then be updated to include both the original data points and data points from the subsequent exposures to progressively improve the accuracy of the surface model.

The ability to analyse off-axis wavefront data from a sample can also be useful for designing or prescribing contact lenses or spectacles that would correct a myopic patient's refractive power in the central on-axis wavefronts while ensuring that the peripheral wavefronts are focused on or behind the retina, thus preventing or reducing myopic progression. Furthermore the patient's eye(s) could be imaged again with the corrective lens(es) in place to confirm that the lenses are performing as required, or to monitor myopic progression.

The techniques described above with reference to FIG. 9 can also be used to measure the optical depth of an eye (i.e. the length, in terms of the number of optical cycles of the central wavelength, from the first reflection point of the eye under test to the retinal reflection) if the coherence length of the source (as determined by the length over which interference effects can be detected) is suitably long. One approach to enhancing coherence length in low coherence interferometry is discussed with reference to FIG. 10. An optical source 1003 such as a LED or semiconductor optical amplifier with an intrinsic spectral width 1010 of several tens of nm is first filtered with an apparatus comprising a collimating lens 1004, an etalon 1005 and a mirror 1006 in a collimated section of the beam having a path length related to the desired wavelength spacing of the spectral sampling points. The coherence length of the resultant output beam 1007 is inversely proportional to the spectral width of each wavelength component 1011 of the output beam. In the specific example shown in FIG. 10 the reduction in spectral width from 40 nm to 0.02 nm will yield a 200× enhancement in coherence length. As such, even a moderately low finesse etalon can provide significant enhancement of the range over which measurable fringes can be detected.

An alternative to the use of an etalon is to employ an optical delay apparatus, comprising for example beam splitters and combiners, to provide different path lengths, wherein the optical delay is chosen to provide simultaneously coherence at, say, the front surface of the eye and at the retina. This delay could also be included at different positions in the instrument in either the sample or reference beams.

Figure 10:
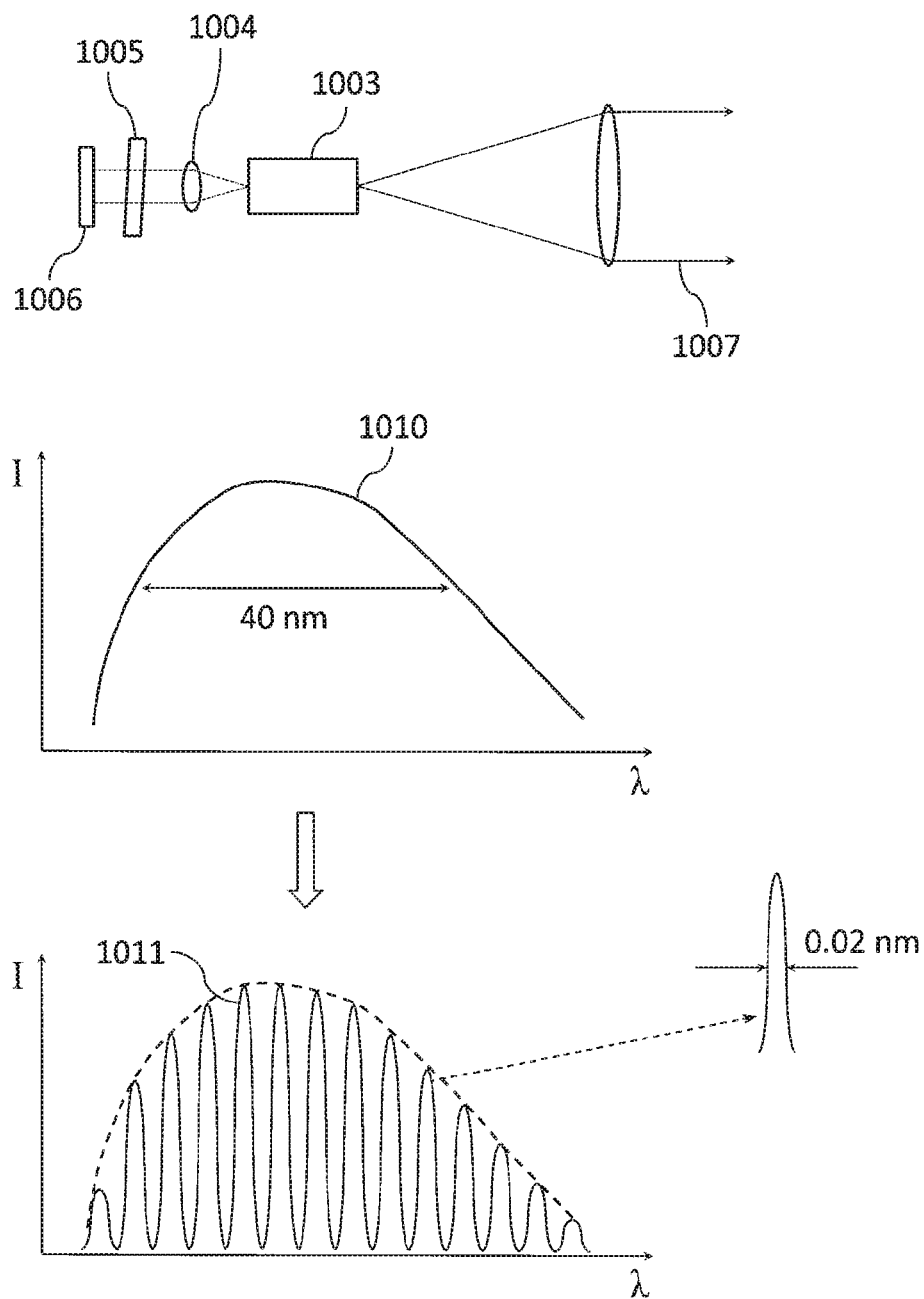
FIG. 10 illustrates a technique for enhancing path length coherence in low coherence interferometry.

The surface registration techniques described with reference to the optical relay system of FIG. 10 can also be used to register data from multiple exposures acquired with different delay path lengths, provided that both sets of data include a common reference surface. This approach could be used, for instance, to register a data set containing the anterior and posterior surfaces of the cornea and lens with another data set containing the anterior corneal surface and the retina. Accurate measurement of all the optically significant surfaces of an eye, relative to a common reference, means that it is possible to reconstruct the ocular wavefront along any axes by performing a simulated ray tracing technique, assuming average population values for the refractive indices of the cornea, lens, aqueous humour and vitreous body. For ocular applications focusing on the sparse reflections from various interfaces in an eye, this can allow simultaneous measurement of the front surface and retina for example. However the under-sampling of the spectrum may lead to ghost images and artefacts.

In the above-described embodiments the wavefront being analysed is obtained by reflection from a sample under test, such as an eye. However it will be appreciated that the wavefront could also be obtained by transmission through a sample under test. In either case, information on the sample is encoded in the shape and spectral composition of the wavefront. It will be appreciated that the illustrated embodiments enable one to extract optical phase and spectral information such as phase and amplitude data as a function of wavelength at multiple sampling points across a wavefront reflected from a sample. Relative phase information between the sampling points is maintained, and the resulting phase accuracy can be exploited to provide systems and methods for making accurate measurements relying on optical phase in eyes and other living biological samples which may be prone to motion artefacts.

Although the invention has been described with reference to specific examples, it will be appreciated by those skilled in the art that the invention may be embodied in many other forms.

What is claimed is:

1. A method for analyzing a sample, said method comprising the steps of:
   (a) forming, from a multi-wavelength wavefront, a plurality of probe beams and one or more reference beams;
   (b) simultaneously directing said probe beams onto a two-dimensional array of points on said sample;
   (c) passing, through a microlens array or an aperture array, a plurality of signals obtained by reflection or transmission of said probe beams from or through said sample;
   (d) extracting phase and spectral information from said signals, said phase and spectral information comprising phase relative to said one or more reference beams as a function of wavelength; and
   (e) processing the extracted phase and spectral information to provide a tomographic profile of said sample at each of said points.

2. The method according to claim 1, wherein said plurality of probe beams is formed by one or more microlens arrays.

3. The method according to claim 1, wherein said phase and spectral information is extracted from said plurality of signals in a single acquisition, to reduce artefacts caused by motion of said sample.

4. The method according to claim 1, wherein said tomographic profile comprises the profile of two or more interfaces in the anterior segment of an eye.

5. The method according to claim 4, wherein said two or more interfaces include the anterior surface of the cornea of said eye.

6. The method according to claim 1, wherein said optical phase and spectral information is extracted by interfering said plurality of signals with said one or more reference beams.

7. The method according to claim 1, wherein said probe and reference beams are orthogonally polarized, and said method further comprises the step of analyzing a first polarization state after said signals have been recombined with said one or more reference beams.

8. The method according to claim 7, wherein more than one polarization state is analyzed to provide balanced detection of said signals.

9. The method according to claim 1, wherein step (a) comprises forming a plurality of probe beams and a like plurality of reference beams.

10. The method according to claim 1, further comprising the step of passing said multi-wavelength wavefront through an etalon to enhance the coherence length of the light in said probe and reference beams.

11. An apparatus for analyzing a sample, said apparatus being configured to:

form, from a multi-wavelength wavefront, a plurality of probe beams and one or more reference beams;

simultaneously direct said probe beams onto a two-dimensional array of points on said sample;

pass, through a microlens array or an aperture array, a plurality of signals obtained by reflection or transmission of said probe beams from or through said sample;

extract phase and spectral information from said signals, said phase and spectral information comprising phase relative to said one or more reference beams as a function of wavelength; and process the extracted phase and spectral information to provide a tomographic profile of said sample at each of said points.

12. The apparatus according to claim 11, wherein said apparatus comprises one or more microlens arrays for forming said plurality of probe beams.

13. The apparatus according to claim 11, wherein said apparatus is configured to extract phase and spectral information from said plurality of signals in a single acquisition, to reduce artefacts caused by motion of said sample.

14. The apparatus according to claim 11, wherein said tomographic profile comprises the profile of two or more interfaces in the anterior segment of an eye.

15. The apparatus according to claim 14, wherein said two or more interfaces include the anterior surface of the cornea of said eye.

16. The apparatus according to claim 11, wherein said apparatus is configured to extract said optical phase and spectral information by interfering said plurality of signals with said one or more reference beams.

17. The apparatus according to claim 11, wherein said apparatus comprises polarization optics for orthogonally polarizing said probe and reference beams and for analyzing a first polarization state after said signals have been recombined with said one or more reference beams.

18. The apparatus according to claim 17, wherein said polarization optics are configured to analyze more than one polarization state, to provide balanced detection of said signals.

19. The apparatus according to claim 11, wherein said apparatus is configured to form a plurality of probe beams and a like plurality of reference beams.

20. The apparatus according to claim 11, wherein said apparatus comprises an etalon for enhancing the coherence length of the light in said probe and reference beams.

21. An apparatus for analyzing an eye, said apparatus being configured to:

form, from a multi-wavelength wavefront, a plurality of probe beams and one or more reference beams;

simultaneously direct said probe beams onto a two-dimensional array of points on said eye;

pass, through a microlens array or an aperture array, a plurality of signals obtained by reflection of said probe beams from said eye;

extract phase and spectral information from said signals, said phase and spectral information comprising phase relative to said one or more reference beams as a function of wavelength; and process the extracted phase and spectral information to provide, at each of said points, a tomographic profile comprising the profile of two or more interfaces in the anterior segment of said eye.

* * * * *